United States Patent [19]

Trotel

[11] Patent Number: 5,080,100
[45] Date of Patent: Jan. 14, 1992

[54] SYSTEM AND METHOD FOR MEASURING AND/OR CHECKING THE POSITION OF A PATIENT IN A RADIO-THERAPY MACHINE

[75] Inventor: Jacques Trotel, Palaiseau, France

[73] Assignee: CGR MeV, Buc, France

[21] Appl. No.: 416,310

[22] Filed: Oct. 3, 1989

[30] Foreign Application Priority Data

Oct. 4, 1988 [FR] France ................................. 88 12973

[51] Int. Cl.$^5$ ............................ A61B 6/04; A61B 6/08
[52] U.S. Cl. .................................. 128/653.1; 358/107; 358/111; 378/99
[58] Field of Search ............. 128/653 R; 358/93, 107, 358/111, 903; 378/99

[56] References Cited

U.S. PATENT DOCUMENTS

| | | | |
|---|---|---|---|
| 4,208,675 | 2/1980 | Bajon et al. | 358/93 |
| 4,521,808 | 6/1985 | Ong et al. | 358/111 |
| 4,593,967 | 6/1986 | Haugen | 350/3.71 |
| 4,675,731 | 6/1987 | Takasu et al. | 378/99 |
| 4,679,076 | 7/1987 | Vikterlöf et al. | 358/107 |
| 4,741,621 | 5/1988 | Taft et al. | 358/107 |
| 4,825,393 | 8/1989 | Nishiya | 358/107 |
| 4,853,777 | 8/1989 | Hupp | 358/107 |

FOREIGN PATENT DOCUMENTS 0062941 9/1984 European Pat. Off. .
0205720 9/1986 European Pat. Off. .
1328033 8/1973 United Kingdom .

OTHER PUBLICATIONS

Endo et al., "Patient Beam Positioning System Using CT Images", Phys. Med. Biol., 1982, vol. 27, No. 2, pp. 301-305.

Primary Examiner—Lee S. Cohen
Assistant Examiner—Krista M. Pfaffle
Attorney, Agent, or Firm—Walter C. Farley

[57] ABSTRACT

The disclosure concerns radio-therapy machines and installations. The precise position of a patient is verified by means of a device mounted on the movable arm of a mount with isocentric motion. This device includes a system for scanning by a light beam. The position of the source of this light beam corresponds to the position of radiation source. The device further has a system for the optical detection of the point of impact of the light beam on the patient. These two systems enable the position of the point of impact to be determined by means of a data-processing system.

2 Claims, 2 Drawing Sheets

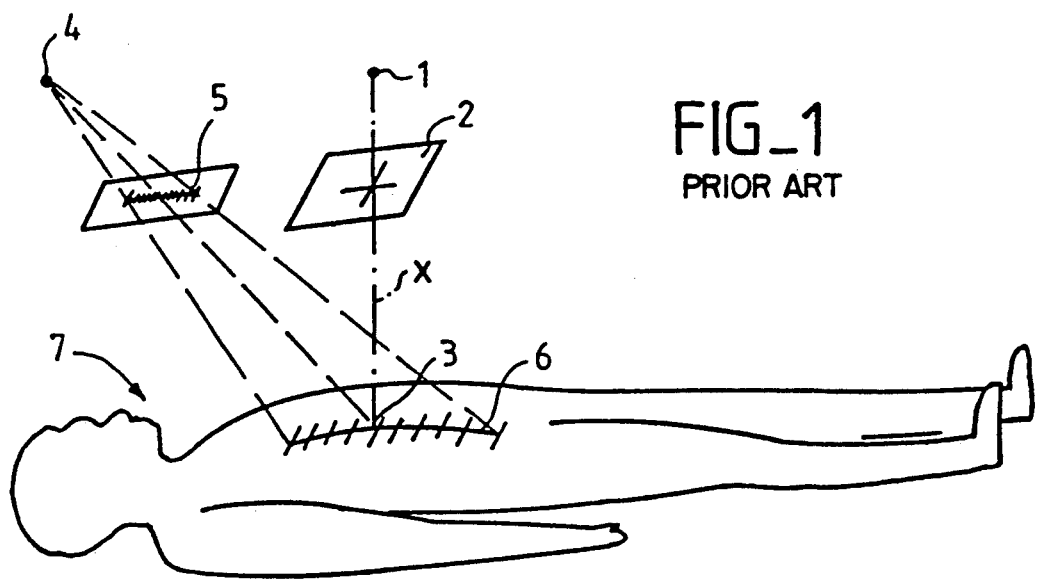
FIG_1
PRIOR ART
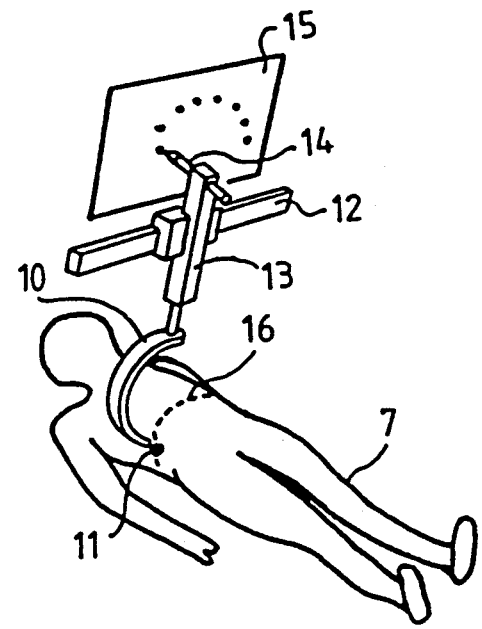
FIG_2
PRIOR ART
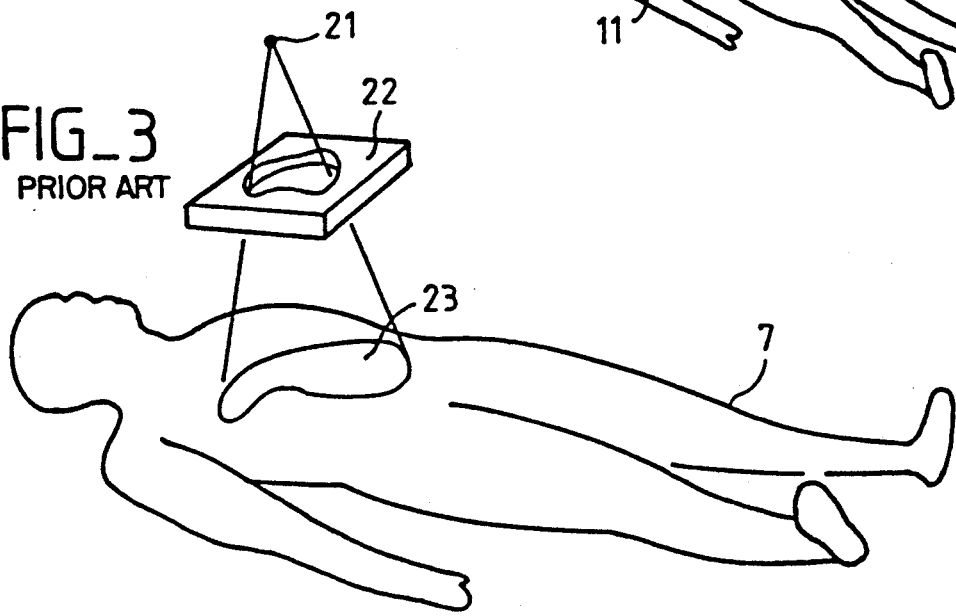
FIG_3
PRIOR ART

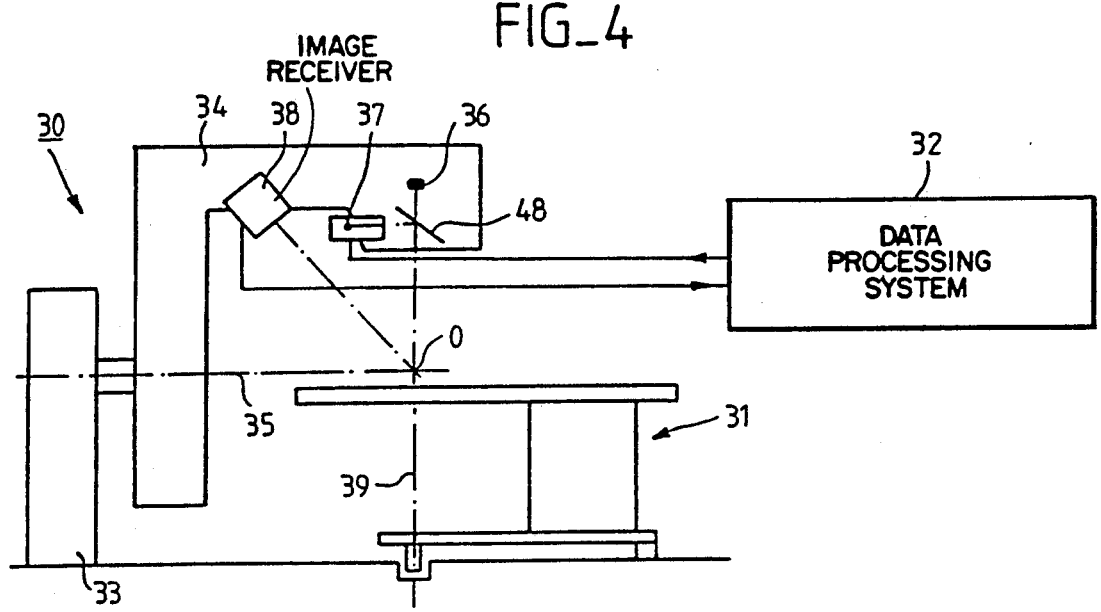
FIG_4
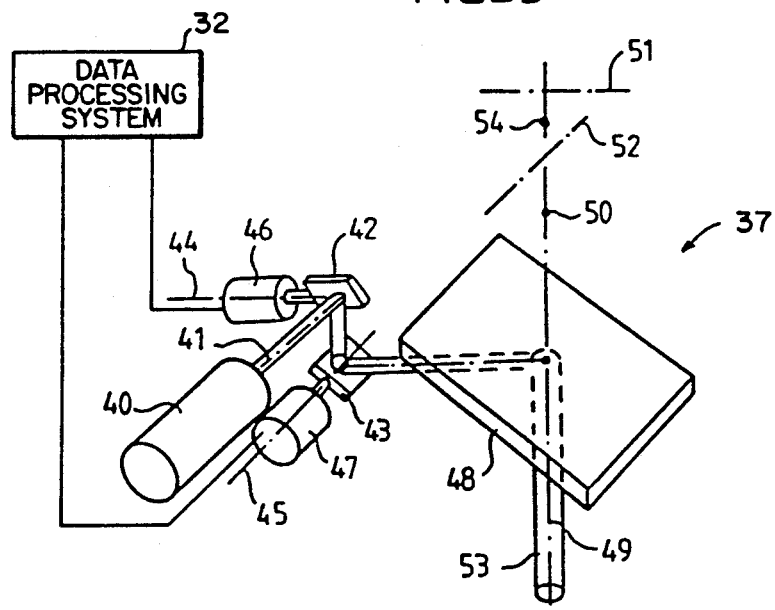
FIG_5

SYSTEM AND METHOD FOR MEASURING AND/OR CHECKING THE POSITION OF A PATIENT IN A RADIO-THERAPY MACHINE

BACKGROUND OF THE INVENTION

1. Field of the Invention

The invention concerns radio-therapy and, more particularly, in a radio-therapy machine, a system and a method for measuring and checking the position of a patient.

2. Description of the Prior Art

Radio-therapy treatment is decided on the basis of a whole set of information of a diagnostic type, essentially comprising information on the nature, extent and location of the tumor and information on the general state of the patient. The treatment is defined by a program of treatment which is drawn up so as to give a prescribed dose of radiation to the volume of the tumor and the smallest possible dose to tissues that do not form part of the volume of the tumor. To this effect, the treatment program defines the nature, intensity, orientation and extent of the beams which will be used to irradiate the patient, and is drawn up on the basis of geometrical data given by a simulator and results of computations of doses given by a specialized data processing system.

The radio-therapy simulator essentially consists of a radiology apparatus using X-rays, which reproduces the geometry of the radio-therapy apparatus but uses a diagnostic type of X-ray source, namely one with low energy compared with that of the high energy radiation source of the radio-therapy apparatus. This radio-therapy apparatus is associated with an imaging system used to display the organs and tissues that the X-ray beam goes through.

To treat the tumor, it is necessary to have precise knowledge of its position with respect to the radiation source. For this purpose, the simulator has several optical means to identify the relative position of the patient and the radiology apparatus. One of these means is a telemeter designed to measure the distance between the X-ray source and the point at which the axis of the X-ray beam enters the patient's body. This distance is called the source-skin distance.

As shown in FIG. 1, a telemeter of the type used in a radio-therapy simulator has a first light source which projects the shadow of a cross 2 on a patient 7. The light source 1 is merged with the X-ray source and the point of intersection of the two arms of the cross 2 is located on the axis of the beam X. The point 3, the projected shadow, on the patient's skin, of the intersection point of the two arms of the cross 2, is therefore merged with the point at which the axis of the beam X enters the body of the patient 7.

The telemeter also has a second light source 4 which projects the shadow of a graduated scale 5 on the patient 7. The source 4 and the axis of the graduated scale 5 are in the same plane as the axis of the X-ray beam and the result thereof is that the axis of the shadow 6 of the graduated scale 5 goes through the point 3.

The point marking the shadow of the graduated scale 5, which coincides with the point 3, depends on the distance between the source 1 and the point 3 so that the observation of this marker point in coincidence with the point 3 thus gives a measurement of the source-skin distance.

The data used by a computer system to compute the doses comprises, firstly, the geometry and the nature of the beams and, secondly, information on the patient's anatomy in the region exposed to the radiation.

The anatomical information is generally given in the form of images representing the density of the patient's tissues in the coronal sections of the patient. The images of these sections are given by several means:

- the radiology apparatus of the simulator which gives views at a variety of angles of incidence;
- a tomodensitometer which gives information on the nature of the tissues and;
- a conformator or shape plotting apparatus which gives readings of the external contour of the patient in different sectional planes.

FIG. 2 enables an understanding of what a conformator consists of. It has a tracer 10, the tip of which can move only in a plane defined by two moving rails 12 and 13. This plane is brought into coincidence with the plane of the section for which it is sought to plot the external contour. The tracer 10 is provided, at the end opposite its tip 11 with a pencil 14 designed to trace points on a sheet of paper 15 placed in a plane parallel to the section plane. It will be understood that, by construction, the movement of the pencil 14 is deduced, by translation, from that of the tip 11. Thus, to read an external contour 16, the tip 11 of the tracer 10 is brought into contact with some significant positions on the skin of the patient 7 and, for each of these positions, a point is traced by the pencil 14 on the sheet 15.

The various operations that have just been briefly described enable the radio-therapy treatment program to be drawn up. To implement it, it is necessary to define the relative position of the different X-ray beams, stipulated by the treatment, with respect to the patient's body. This is obtained by drawing indelible marks on the patient's skin so as to indicate the contour of each X-ray beam. To enable these various marks to be drawn, the X-ray beams are displayed by optical means called delineators.

A delineator (FIG. 3) consists of a light source 21, placed at the point of origin of the X-ray beam which projects the shadow of a diaphragm 22 on the patient's skin. The shape of the diaphragm is such that its projection 23 on the patient's skin represents the plotting of the entrance of the X-ray beam into the patient and is used to draw the identifying marks on the patient's skin.

The diaphragm 22 usually consists of a set of movable plates, with rectilinear edges when the beam is rectangular, or a specially cut plate when the beam has a more complex shape.

When the operations that have just been described are over, the patient can be treated in a radio-therapy installation. The first operation of the treatment consists in placing him in a position that corresponds, as far as possible, to the one he had in the simulator. To this effect, this radio-therapy installation has several optical means corresponding to those of the simulator, in particular the telemeter.

Before the patient is subjected to irradiation, the position of the therapeutic beams with respect to the patient is verified with a delineator identical to that of the simulator so as to make sure that the light trace thus obtained corresponds to the marks made on the patient's skin.

The following are the main drawbacks of prior art simulation systems:

The measurement of the source/skin distance requires the presence of an operator near the patient to observe the light traces projected by the telemeter. The result thereof is a loss of time and risks of making mistakes. But, above all, the measurement cannot be made during the irradiation because the operator cannot stay near the patient. This means that involuntary movements by the patient are not detected and may thus result in irradiation that is not according to the irradiation program.

The plotting of the external contour of a section of the patient, using a conformator, is a slow operation that lacks precision and calls for the presence of an operator near the patient. It therefore cannot be done during irradiation. This prevents its use as a supplementary means to ascertain that the treatment is with inaccordance with the treatment program.

The program of optical delineation is fast only when the beam has a rectangular section. In the most complicated cases, specific diaphragms have to be made and this is a slow process.

An aim of the present invention, therefore, is to make a system, for the measurement and checking of a patient's position, that does not have the above-mentioned drawbacks of prior art systems, and which fulfils the functions of the telemeter, the conformator and the delineator described above.

SUMMARY OF THE INVENTION

The invention relates to a system for the measurement and/or checking of the position of a patient in a radio-therapy machine having a mount with isocentric motion, a table on which the patient is placed and a radiation source which may be at low energy for simulation operations or at high energy for radio-therapy operations, wherein said system comprises a device for a scan by a light beam along at least one direction, so as to be capable of scanning at least one to control the positions of the light beam so as to shift the light beam along a defined trace on the surface of the patient's body, said trace demarcating the surface of impact of the high energy beam of rays.

The system further comprises a device to detect the impact of the light beam on the patient's body and a computation device, connected to the device that controls the position of the light beam and to the detection device, to compute the position of the impact of the light beam on the patient's body so that it is possible to define, firstly, the distance between the high energy ray source and the surface of the patient's body and, secondly, the external contour of a section of the patient's body.

The invention also relates to a method for the measuring and/or checking of the position of a patient in a radio-therapy machine comprising a mount with isocentric motion, a table on which the patient is placed and a radiation source which may be at low energy for simulation operations or at high energy for radio-therapy operations, said radiation source being borne by the mounting, wherein said method comprises the following operations:

a) a scanning of at least one part of the surface of the patient's body by a light beam, the source of which is merged with the radiation source so as to surface of the patient's body;

b) a detection of these points of impact by the recording of an appropriate image;

c) a computation of the position of these points of impact using the knowledge of the position of the source and the position, on the image, of these points of impact;

d) a recording of the positions of these points of impact with respect to the corresponding positions of the light beam that has given rise to them.

The method further comprises the following operations:

e) scanning the patient's body by the light beam using information on recorded positions of the light beam to obtain the points of impact for which the positions have been recorded;

f) measuring the real position of these points of impact in implementing the operation a), b), c) and d).

g) comparing the real positions of the points of impact with the recorded position, and, h) moving the patient's body so that the real positions coincide with the recorded positions.

BRIEF DESCRIPTION OF THE DRAWINGS

Other features and advantages of the present invention will appear from the following description of a particular exemplary embodiment, said description being made with reference to the appended drawings, of which:

FIG. 1 is a drawing that enables an understanding of the principle of the measurement of the source-skin distance;

FIG. 2 is a drawing that enables an understanding of the working principle of a conformator an external contour of a patient;

FIG. 3 is a drawing that enables an understanding of the working principle of a delineator of the trace of a beam on a patient;

FIG. 4 is a schematic diagram of a system to measure and check the position of a patient in a radio-therapy machine according to the invention, and FIG. 5 is a perspective view of an optical scanning device which can be implemented to make the system according to the invention.

DESCRIPTION OF PREFERRED EMBODIMENTS

FIGS. 1 to 3, which have been used to explain the working principle of the telemeter, the conformator and the delineator of the prior art, respectively, shall not be described again.

FIG. 4 shows a medical equipment which may be both a radio-therapy apparatus and a system to measure and check the position of a patient. This equipment has a mounting 30, a patient-supporting table 31 and a computer or data processing system 32. The mounting 30 is of the type with isocentric motion and can be made in different known ways. It has, for example, a pedestal 33 that supports an L-shaped arm 34. This arm can rotate around a horizontal axis 35. That part of the arm which is on top of the table 31 acts as a support for a certain number of elements, namely an X-radiation source or ionizing radiation source 36, a light scanning device 37 and an image receiver 38. The scanning device 37 and the image receiver 38 are connected to data processing system 32. The table 31 is designed to be shifted along different axes so as to adjust the position of the patient with respect to the mounting. For example, the motions that can be performed by the table are a vertical translational motion, a horizontal translational motion and a rotational motion on a vertical axis 39 that coincides with the axis of radiation of the source 36 when the latter is in the plane of FIG. 4. It must be noted that, in FIG. 4, the isocenter is designated by the letter 0.

In a radio-therapy installation, the radiation source 36 gives high energy radiation. In a radio-therapy simulator, the radiation source 36 gives low energy X-radiation and is designed to work with a receiver (not shown in FIG. 4) located on the other side of the patient with respect to the source.

FIG. 5 shows an exemplary embodiment of the light scanning device 37. It has a light source 40, preferably a laser source, which emits a narrow beam of visible light 41. It also has two rotating mirrors 42 and 43 which respectively oscillate on axes 44 and 45, one of which (44) is perpendicular to the axis of the light beam 41, which it receives directly, while the other is perpendicular to the former and parallel to the axis of the beam 41. The scillation of these mirrors 42 and 43 is obtained respectively by galvanometric deflectors or motors 46 and 47 controlled by the data processing system 32.

The light beam 41 is reflected by these two mirrors 42 and 43 to be sent to a third fixed mirror 48 which reflects it towards the patient's body along an axis 49 in the resting position of the mirrors 42 and 43. This axis 49 coincides with the central axis of radiation 50 of the radiation source 36. The mirror 48 is transparent to the radiation used.

The oscillatory motions of the mirror 42 produce an oscillation of the beam 41 around an axis 51 which is deduced from the axis 44 by a first symmetry with respect to the mirror 43 and then by a second symmetry with respect to the mirror 48.

The oscillatory motions of the mirror 43 produce an oscillation of the beam 41 around an axis 52 which is deduced from the axis 45 by a symmetry with respect to the mirror 48.

If the mirrors 42 and 43 are very close to each other, the same will be the case for the axes 51 and 52 and the combined motions of the mirrors 42 and 43 will appreciably produce an oscillation motion of the beam 53 around a point 54 located on the perpendicular common to the axes 51 and 52 and at equal distance from these two axes.

Preferably, the mirrors 42, 43 and 48 are arranged in such a way that the point 54 is merged with the X-ray source point in the case of the simulator or the high energy source, X-rays or other high energy rays, in the case of a radio-therapy machine.

Preferably, again, the axes 51 and 52 are perpendicular to each other and perpendicular to the axis 50 of the X-ray beam (or the beam of high-energy rays) and one of the axes 51 or 52 is parallel to the axis of rotation 35 of the arm 34 (FIG. 4).

The scanning device 37 can be used to make the light beam 41 describe the external surface of the X-ray or high energy beam, depending on the signals applied to the deflectors 46 and 47. The trace of the beam 53 on the patient's skin then represents the boundaries of the trace of the X-ray or high energy beam when it enters the patient. It is thus possible to achieve the function of a delineator without having to make a diaphragm as in the prior art.

During the simulation operations, the scanning of the beam 53 is activated by the operator to obtain the trace marked on the patient's body. The items of control data are recorded in a memory and then used on the scanning device of the radio-therapy apparatus, to thus obtain the same trace on the patient as the indelible marking, by moving the latter so that this is what happens.

The scanning device that has been described as an example has two oscillating mirrors, but it is possible to do the same scanning with only one mirror which would be driven by motions along two perpendicular axes.

In order to fulfil the functions of the conformator and the telemeter of the prior art, the invention provides for associating the image receiver 38 with the scanning device 37. This image receiver 38 is designed to give a plane image of the entire region of the space where the point of impact of the light beam 53 might be located on the patient's skin. Using this image of the point of impact and the geometrical data on the orientation and position of the beam 53 and of the receiver, it is possible to determine the position in space of the point of impact of the light beam 53 on the patient's body.

Devices of this type are known and are described, for example, in the U.S. Pat. No. 4,593,967.

In shifting the light beam on the patient's skin, a three-dimensional reading is obtained of the external surface of the patient which may be reached by the light beam for a certain angular position of the arm 34. With different angular positions of the arm 34, it is possible to have practically a reading of the external surface of the patient which is of use for radio-therapeutic treatment.

In a reading such as this, the measurement of the skin/source distance is only a particular example corresponding to the light beam 53 merged with the axis 50 of the X-ray or high energy beam. The device therefore fulfills the function of the telemeter.

The reading of the external contour of a section of the patient is also only a particular example corresponding to the reading of several points for positions of the light beam contained in a plane perpendicular to the axis of rotation 35 of the arm 34.

The system according to the invention has been described with reference to a light scanning device 37 and an image receiver 38 which are mounted on the arm 34 of the mounting 30.

However, the device can be implemented with a light scanning device and an image receiver which would be mounted on a support which is independent of that bearing the X-ray or high energy source 36 provided that the position of the light beam and that of the image receiver are known and given to the data processing system 32. Furthermore, the oscillation point 54 of the light beam should be capable of being put into coincidence with the X-rays or high energy source to fulfill the function of the delineator.

In the description of the light scanning device, it has been stated that the light beam 41 or 53 is narrow, but it may have the form of a plane beam. In this case, the function of the delineator is fulfilled with greater difficulty, but the function of the conformator is fulfilled more simply, for all the points of the external contour of a section of the patient by the plane of the light beam simultaneously give an image upon the image reception. With a plane light beam such as this, it is enough for a light deflector with only one rotational axis to plot several plane sections.

The image receiver may be, for example, a television camera which gives a digital image and uses an energy analyzing tube or a matrix of photodiodes. A two-dimensional image is then obtained.

It is also possible to use an image receiver which gives an image with only one dimension, and the sensor will then be, for example, a linear strip of photodiodes.

The invention also concerns a method to measure and/or verify the position of a patient with respect to a beam of rays with a view to a radio-therapy treatment.

On the basis of the above description of the system, the following are the operations:

a) The scanning by the light beam 53 of the body of the patient 7 to obtain determined points of impact of the light beam, said points of impact corresponding to the source/skin distance, to a cross-section of the patient or to the contour of the radio-therapy beam on the patient's body;

b) The detection of these points of impact by the image receiver 38 so as to obtain an image of said points;

c) The computation of the coordinates of these points of impact by the data processing device 32 using coordinates of the source 54 and those of the image of the said points; and d) The recording of the coordinates of these points of impact in relation to the corresponding positions of the light beam which has given rise to them.

A part of the operations that have just been described correspond to those performed during simulation in a radiological apparatus of the diagnostic type. The data resulting therefrom is used with the data collected by means of the radiological apparatus and the tomodensitometer to define the treatment program for the patient. This program defines, in addition to the intensity of the radio-therapy beam and the time of exposure, the relative positions of the different radio-therapy beams with respect to the body of the patient and their respective contours on the body of the patient, so as to obtain traces on the body of the patient. These different traces are scanned by the light beam 53 in performing the operations a), b), c), and d), described above, thus enabling the obtaining and recording of the coordinates of the traces with respect to the positions corresponding to the light beam which has given rise to them. It is these items of data that will be used in the radio-therapy apparatus to reposition the patient's body, with respect to the different beams according to a comparative process comprising the following operations:

e) the scanning of the patient's body by the light beam, using data on the position of the light beam which has been recorded so as to obtain the points of impact for which the coordinates have been recorded.

f) The measurement of the real position of these points of impact using operations a), b), c), and d), which have been described above, to thus obtain the real coordinates of the points of impact;

g) The comparison of the real coordinates of the points of impact with the recorded coordinates so as to determine whether or not there is a deviation and, h) The shifting of the patient's body, so that the real positions coincide with the recorded positions.

In certain cases, it may be simpler for the operations f), g) and h) to be done visually by the operator, in comparing the trace obtained by a repetitive scanning of the light beam according to the recorded information on the position of the beam with the contour marked out on the patient's body.

What is claimed is:

1. A method for measuring and checking the position of a patient in a radio-therapy machine having a radiation source and a mount for supporting the radiation source for isocentric motion, the method comprising the steps of
    (a) positioning the patient on a support surface,
    (b) scanning a region of the surface of the patient's body with a pivotable light beam having a pivot center which has a known spatial relationship with the radiation source to create a plurality of light spots at a first set of points of incidence,
    (c) detecting and recording images of the first set of points of incidence of the spots on the surface region,
    (d) computing the coordinates of the first set of points of incidence relative to the radiation source and relative to the corresponding positions of the light beam,
    (e) subsequently scanning substantially the same region of the patient's body with the light beam using information on the recorded first set of points of incidence to recreate a plurality of spots of light at a second set of points of incidence corresponding to the first set,
    (f) detecting the images of the second set of points,
    (g) determining the coordinates of the second set of points and comparing the coordinates of the second set of points with the coordinates of the first set of points, and
    (h) if there are differences between the coordinates of the first and second sets of points, repositioning the patients body until the coordinates substantially coincide.

2. A system for measuring and checking the position of a patient in a radio-therapy machine having a radiation source and a mount for supporting the radiation source for isocentric motion, comprising the combination of
    (a) a support surface for holding the patient,
    (b) means including a pivotable light beam for scanning a region of the surface of the patient's body to create a plurality of light spots at a first set of points of incidence, said beam having a pivot center at a known spatial location relative to the radiation source;
    (c) means for detecting and recording images of said first set of points of incidence of the spots on the surface region;
    (d) means for computing the coordinates of said first set of points of incidence relative to the radiation source and relative to corresponding positions of the light beam,
    (e) means for detecting images of a second set of points subsequently produced by said light beam,
    (g) means for determining the coordinates of said second set of points and comparing the coordinates of said second set of points with the coordinates of said first set of points, whereby, if there are differences between the coordinates of said first and second sets of points, the patients body can be repositioned until said coordinates substantially coincide.

* * * * *